United States Patent
Schreiter et al.

(10) Patent No.: US 11,708,397 B2
(45) Date of Patent: Jul. 25, 2023

(54) CHEMIGENETIC CALCIUM INDICATORS

(71) Applicant: HOWARD HUGHES MEDICAL INSTITUTE, Chevy Chase, MD (US)

(72) Inventors: Eric R Schreiter, Ashburn, VA (US); Luke D. Lavis, Leesburg, VA (US); Claire Deo, Ashburn, VA (US); Hersh Bhargava, Berkeley, CA (US); Ahmed Abdelfattah, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 333 days.

(21) Appl. No.: 16/768,153

(22) PCT Filed: Dec. 31, 2018

(86) PCT No.: PCT/US2018/068160
§ 371 (c)(1),
(2) Date: May 29, 2020

(87) PCT Pub. No.: WO2019/133976
PCT Pub. Date: Jul. 4, 2019

(65) Prior Publication Data
US 2020/0317743 A1    Oct. 8, 2020

Related U.S. Application Data

(60) Provisional application No. 62/611,666, filed on Dec. 29, 2017.

(51) Int. Cl.
*C07K 14/47* (2006.01)
*G01N 33/58* (2006.01)
(Continued)

(52) U.S. Cl.
CPC ...... *C07K 14/4728* (2013.01); *A61K 49/0004* (2013.01); *A61K 49/0041* (2013.01);
(Continued)

(58) Field of Classification Search
CPC ............ C07K 14/4728; C07K 2319/20; C07K 2319/60; C07K 2319/00; A61K 49/0004;
(Continued)

(56) References Cited

U.S. PATENT DOCUMENTS

| 9,644,007 B2 * | 5/2017 | Kim ................... G01N 33/5041 |
| 2009/0215106 A1 * | 8/2009 | Pribilla ................ G01N 33/542 |
| | | 435/29 |

FOREIGN PATENT DOCUMENTS

| WO | WO-2015007317 A1 * | 1/2015 | ............... C12Q 1/66 |
| WO | WO-2018219953 A1 * | 12/2018 | ............... C07K 5/10 |

OTHER PUBLICATIONS

Meador et al. "Target enzyme recognition by calmodulin: 2.4 A structure of a calmodulin-peptide complex." Science, vol. 257, 5074 (1992): 1251-5. (Year: 1992).*
(Continued)

*Primary Examiner* — Bao-Thuy L Nguyen
*Assistant Examiner* — Alexander Alexandrovic Volkov
(74) *Attorney, Agent, or Firm* — Stites & Harbison, PLLC; Mandy Wilson Decker

(57) ABSTRACT

A chemigenetic calcium indicator and a method of measuring calcium are provided. The chemigenetic calcium indicator includes a calcium-binding protein domain attached to a ligand binding protein domain. The method of measuring calcium includes administering a chemigenetic calcium indicator to a subject and determining changes in fluorescence, the chemigenetic calcium indicator including a ligand binding protein domain having a calcium-binding protein domain and a dye-ligand conjugate attached thereto.

14 Claims, 7 Drawing Sheets

Specification includes a Sequence Listing.

(51) Int. Cl.
*G01N 33/84* (2006.01)
*G01N 21/77* (2006.01)
*A61K 49/00* (2006.01)

(52) U.S. Cl.
CPC ......... *A61K 49/0056* (2013.01); *G01N 21/77* (2013.01); *G01N 33/582* (2013.01); *G01N 33/84* (2013.01); *C07K 2319/20* (2013.01); *C07K 2319/60* (2013.01); *G01N 2021/7786* (2013.01); *G01N 2333/4727* (2013.01)

(58) Field of Classification Search
CPC ........... A61K 49/0041; A61K 49/0056; G01N 21/77; G01N 33/582; G01N 33/84; G01N 2021/7786; G01N 2333/4727
See application file for complete search history.

(56) References Cited

OTHER PUBLICATIONS

Kurokawa, et al. "Target-induced conformational adaptation of calmodulin revealed by the crystal structure of a complex with nematode Ca(2+)/calmodulin-dependent kinase kinase peptide." Journal of molecular biology vol. 312,1 (2001): 59-68. (Year: 2001).*

Akerboom et al. "Genetically encoded calcium indicators for multi-color neural activity imaging and combination with optogenetics." Frontiers in molecular neuroscience vol. 6 2. Mar. 4, 2013 (Year: 2013).*

* cited by examiner

CHEMIGENETIC CALCIUM INDICATORS

RELATED APPLICATIONS

This application claims the benefit of U.S. Provisional Application Ser. No. 62/611,666, filed Dec. 29, 2017, the entire disclosure of which is incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Dec. 27, 2018, is named 18074N-18016W.txt and is 38 kilobytes in size.

TECHNICAL FIELD

The presently-disclosed subject matter generally relates to calcium indicators and methods of use thereof. More specifically, the presently-disclosed subject matter relates to chemigenetic calcium indicators and methods of measuring calcium using chemigenetic calcium indicators.

BACKGROUND

Genetically encoded fluorescent calcium indicators (GECI) have become useful reagents for imaging the activity of neurons in the brains of live organisms, in addition to other applications.[1] GECIs use fluorescent protein domains as the fluorescent reporter combined with calcium-binding protein domains in a single polypeptide molecule. Conformational change upon calcium binding alters the fluorescence output of the fluorescent protein domains. However, fluorescent proteins can have limited brightness, photostability, and spectral range, and are generally exceeded by small molecule synthetic fluorophores.

Accordingly, there remains a need for imaging reagents that provide increased brightness, photostability, and/or spectral range.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Provided herein, in some embodiments, is a chemigenetic calcium indicator comprising a calcium-binding protein domain attached to a ligand binding protein domain. In some embodiments, the ligand binding protein domain comprises HaloTag, SNAP-tag, TMP-tag, βLac-tag, CLIP-tag, or a combination thereof. In some embodiments, the ligand binding protein domain comprises a non-covalent capture protein selected from the group comprising a TMP-tag, a biotin-avidin, and a combination thereof. In some embodiments, the calcium binding protein domain comprises calmodulin and a calmodulin binding peptide. In some embodiments, the calcium indicator comprises a DNA sequence according to SEQ ID NO: 1, SEQ ID NO: 3, SEQ ID NO: 5, SEQ ID NO: 7, SEQ ID NO: 9, or SEQ ID NO: 11.

In some embodiments, the chemigenetic calcium indicator further comprises a dye-ligand conjugate attached to the ligand binding protein. In some embodiments, the dye-ligand conjugate comprises a HaloTag ligand conjugated to a fluorescent dye. In some embodiments, the fluorescent dye is selected from the group comprising azetidine-containing Janelia Fluor dyes and rhodamines.

Also provided herein, in some embodiments, is a method of measuring calcium, the method comprising administering a chemigenetic calcium indicator to a subject and determining changes in fluorescence, the chemigenetic calcium indicator comprising a ligand binding protein domain having a calcium-binding protein domain and a dye-ligand conjugate attached thereto. In some embodiments, the ligand binding protein comprises HaloTag and the dye-ligand conjugate comprises a HaloTag ligand conjugated to a fluorescent dye.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2 shows an image of nucleotide and amino acid sequence of chemigenetic calcium indicator with sequence features annotated, according to an embodiment of the disclosure.

DESCRIPTION OF EXEMPLARY EMBODIMENTS

Figure 1:
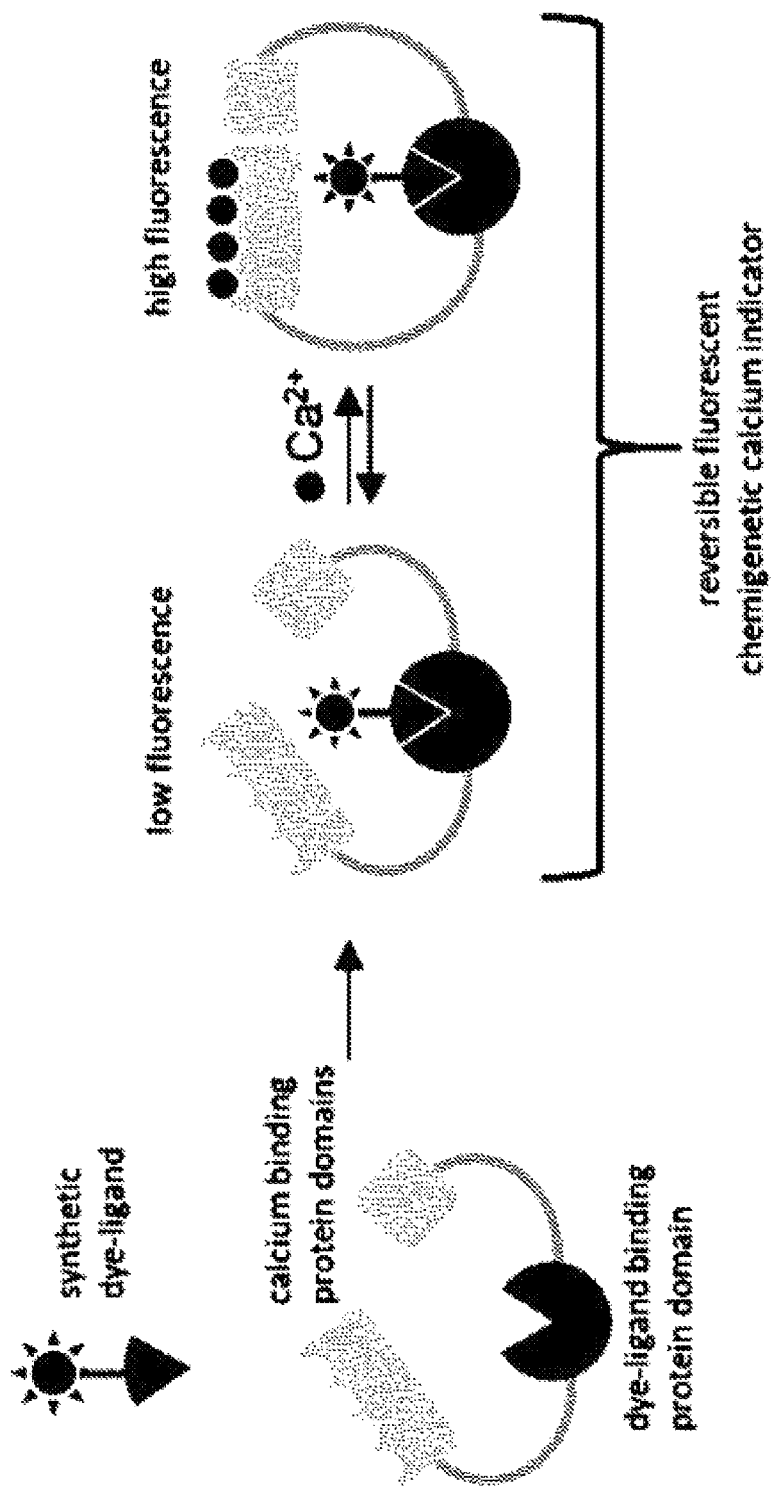
FIG. 1 is a schematic representation of the chemigenetic calcium indicators according to an embodiment of the disclosure.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes calcium indicators and methods of making and using calcium indicators. In some embodiments, the calcium indicators include calcium sensitive fluorophores. For example, in one embodiment, the calcium indicators include a dye-ligand conjugate attached to a ligand binding protein domain (FIG. 1). In another embodiment, attachment of the dye-ligand conjugate to the ligand binding protein domain includes covalent attachment of the dye-ligand conjugate to the ligand binding protein domain. In a further embodiment, the calcium indicators include calcium-binding protein domains attached to the ligand binding protein domain (FIG. 1). This hybrid protein-small molecule including the calcium-binding protein domains attached to the ligand binding protein domain is referred to herein as a "chemigenetic" calcium indicator.

The ligand binding protein domain, or capture protein, includes at least one suitable protein configured to bind the ligand of the dye-ligand conjugate. In some embodiments, the capture protein includes at least one covalent capture protein. For example, in one embodiment, the covalent capture protein includes HaloTag, a modified bacterial haloalkane dehalogenase. In another embodiment, the covalent capture protein includes SNAP-tag. Other suitable covalent capture proteins include, but are not limited to, TMP-tag, βLac-tag, CLIP-tag, or a combination thereof. Additionally or alternatively, the capture protein may include at least one non-covalent capture proteins which capture, or bind, the desired ligand with non-covalent interactions. Suitable non-covalent capture proteins include, but are not limited to, certain TMP-tag, biotin-avidin, or a combination thereof. Although described primarily with regard to a single capture protein, as will be appreciated by those skilled in the art the disclosure is not so limited and may include more than one capture protein, such as multiple covalent capture proteins, multiple non-covalent capture proteins, or a combination of at least one covalent capture protein and at least one non-covalent capture protein.

Figure 2:
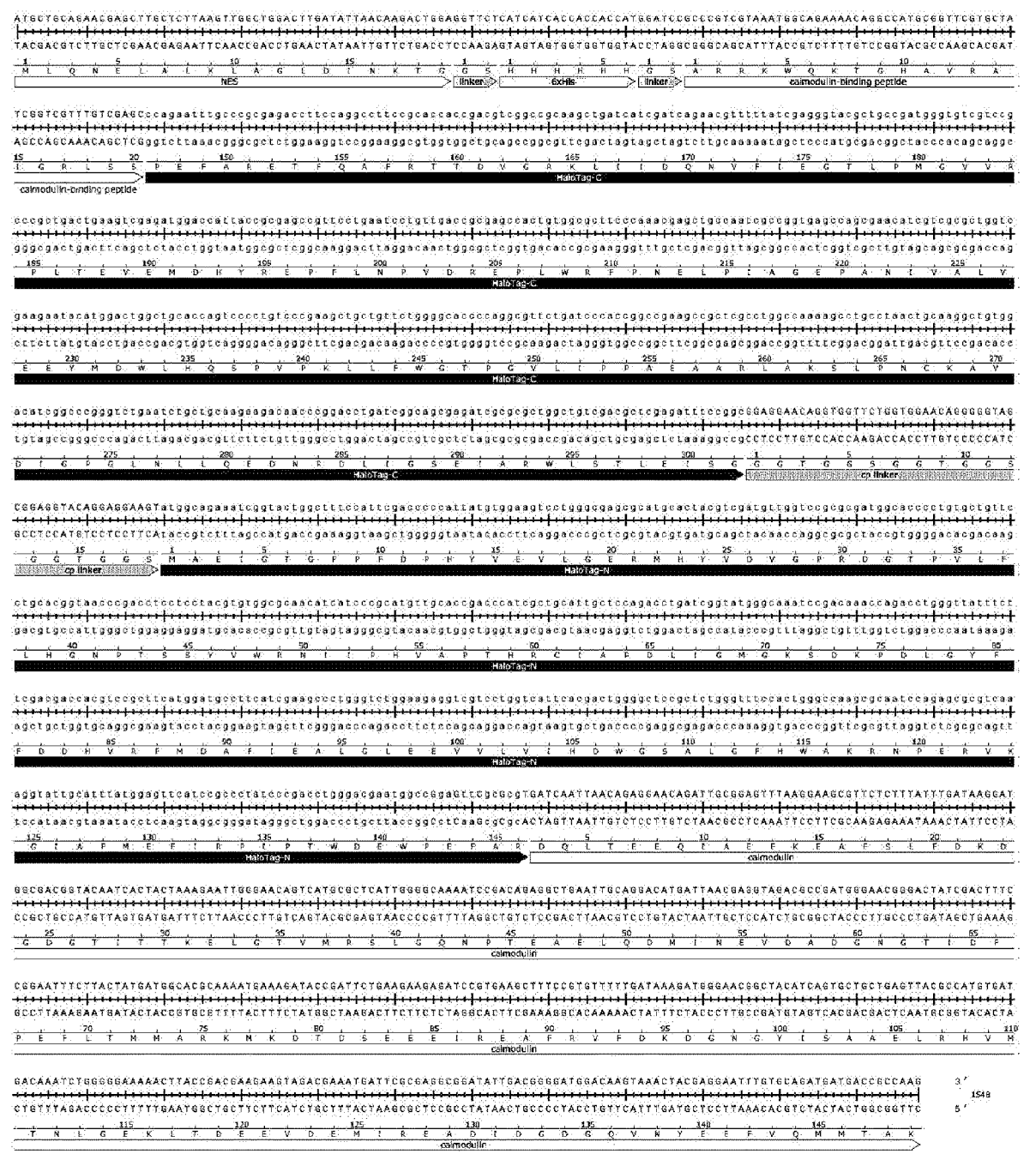

The calcium binding protein domains include any suitable domain or domains for binding calcium and influencing the fluorescence of the dye attached to the ligand binding protein domain. For example, in one embodiment, the calcium-binding protein domains include calmodulin and a calmodulin binding peptide. Other calcium-binding protein domains include, but are not limited to, troponin C, calbindin, calretinin, centrin, any other suitable calcium-binding protein, and/or a combination thereof, along with the associated binding peptide(s) (e.g., calretinin binding peptide for calretinin). As will be appreciated by those skilled in the art, the chemigenetic calcium indicator may include any suitable combination of capture proteins and calcium binding protein domains. FIG. 2 shows an example of one such combination (SEQ ID NOs. 1 and 2) that forms a chemigenetic calcium indicator according to one or more of the embodiments disclosed herein. Examples of other such combinations which form the chemigenetic calcium indicator include, but are not limited to, Sv1 (SEQ ID NOs: 3 and 4), A1 (SEQ ID NOs: 5 and 6), C9 (SEQ ID NOs: 7 and 8), C11 (SEQ ID NOs: 9 and 10), and C12 (SEQ ID NOs: 11 and 12).

Additionally or alternatively, in some embodiments, the chemigenetic calcium indicator may include one or more additional domains, such as, but not limited to, a targeting domain, a purification domain, one or more linkers, or a combination thereof. The targeting domain includes any domain for targeting the indicator to a specific location and/or part of a cell. Suitable targeting domains include, but are not limited to, nuclear export signal (NES); nuclear localization signal (NLS); post-synapse targeting domain, such as PSD-95; pre-synapse targeting domain, such as synaptophysin; membrane localization motif, such as prenylation, N-myristoylation, or S-palmitoylation sequences; and/or cellular organelle-targeting motifs, such as a mitochondria-binding domain. The purification domain is for purification and characterization of the indicator, and is not relevant to the function of the indicator itself. Suitable purification domains include, but are not limited to, polyhistamine, chitin-binding protein (CBP)-tag, glutathione-S-transferase (GST)-tag, and/or maltose-binding protein (MBP)-tag. The one or more linkers are for joining various domains within the indicator. Suitable linkers include, but are not limited to, poly-glycine, poly-glycine-serine, poly-glycine-glycine-serine, and/or poly-glycine-glycine-serine-glycine-glycine-threonine (SEQ ID NO: 13). For example, in one embodiment, as illustrated in FIG. 2, the chemigenetic calcium indicator includes an NES domain, a polyhistadine domain, a poly-Gly-Ser linker attaching the NES domain to the polyhistadine domain, a poly-Gly-Ser linker attaching the polyhistadine domain to the calmodulin-binding peptide, and a poly-Gly-Gly-Ser-Gly-Gly-Thr linker attaching a HaloTag C domain to a HaloTag N domain. Although described above with respect to an indicator including each of the additional domains, as will be appreciated by those skilled in the art the disclosure is not so limited and may include any subset of additional domains (e.g., a targeting domain and one or more linkers) or no additional domains.

Figure 3A:
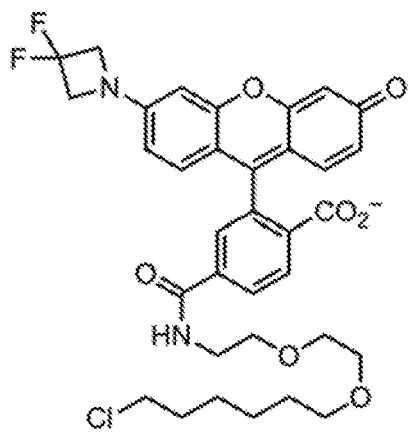
FIGS. 3A-G show chemical structures of various fluorescent dye-ligands according to an embodiment of the disclosure. (A) $JF_{505}$-HaloTag ligand. (B) $JF_{525}$-HaloTag ligand. (C) $JF_{549}$-HaloTag ligand. (D) $JF_{585}$-HaloTag ligand. (E) $JF_{635}$-HaloTag ligand. (F) $JF_{646}$-HaloTag ligand. (G) Tetramethylrhodamine (TMR)-HaloTag ligand.
Figure 3B:
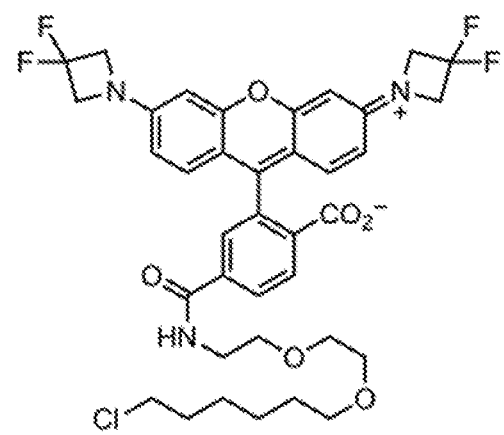
Figure 3C:
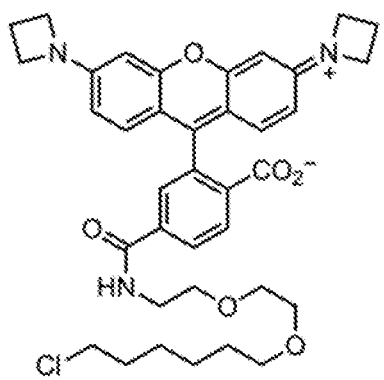
Figure 3D:
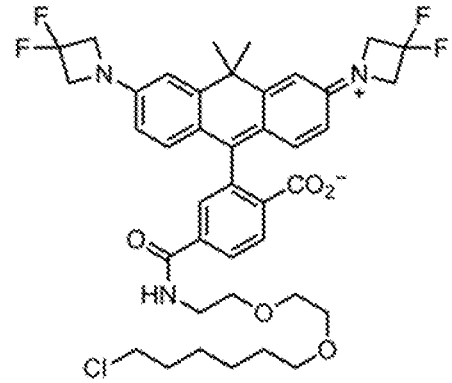
Figure 3E:
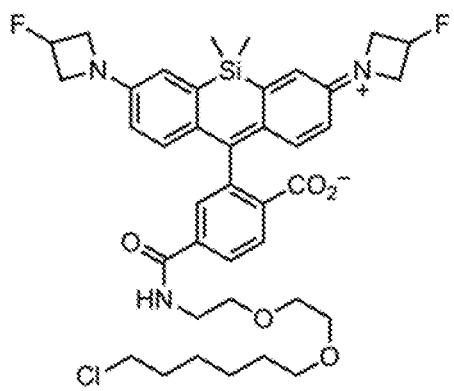
Figure 3F:
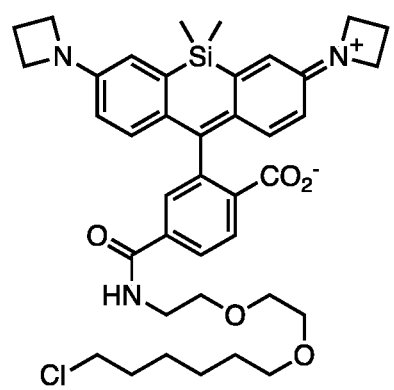
Figure 3G:
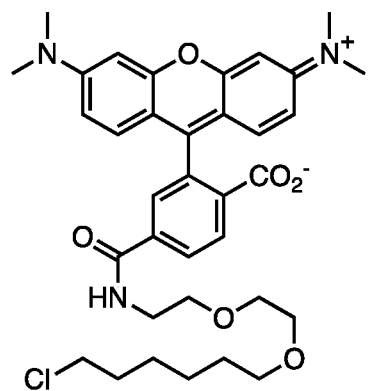

Turning to the dye-ligand conjugate, any suitable dye may be conjugated to any ligand suitable for binding to one or more of the ligand binding protein domains disclosed herein. Suitable dyes include, but are not limited to, fluorescent dyes. In some embodiments, the fluorescent dyes include small-molecule fluorescent dyes such as, but not limited to, one or more fluorophore dyes. In one embodiment, the fluorophore dye includes a fluorophore containing one or more cyclic amine substituents. In another embodiment, the fluorophore dye includes an azetidine-containing rhodamine dye. In a further embodiment, the rhodamine dye includes one or more four-membered azetidine rings in place of the ubiquitous dimethylamino groups of existing fluorophores, forming small, cell-permeable fluorophores having increased brightness and photostability. Such rhodamine dyes include, but are not limited to, Janelia Fluor™$_{505}$, Janelia Fluor™$_{525}$, Janelia Fluor™$_{549}$, Janelia Fluor™$_{585}$, Janelia Fluor™$_{635}$, Janelia Fluor™$_{646}$, and combinations thereof. These dyes are shown in FIGS. 3A-F as attached to a HaloTag ligand. Other suitable dyes include, but are not limited to, rhodamines, such as Tetramethylrhodamine (TMR), which is shown in FIG. 3G as attached to a HaloTag ligand.

As will be appreciated by those skilled in the art, suitable ligands will depend upon the specific ligand binding protein domain being used. Therefore, in some embodiments, the ligand of the dye-ligand conjugate includes any ligand suitable for binding at least one of the ligand binding protein domains disclosed herein. In one embodiment, for example, the ligand includes any suitable ligand for binding HaloTag. Referring to FIGS. 3A-G, in another embodiment, the ligand includes a chloroalkane HaloTag ligand. Other suitable ligands include, but are not limited to, SNAP-tag ligands, TMP-tag ligands, βLac-tag ligands, CLIP-tag ligands, or a combination thereof.

Although one or more of the small molecule synthetic fluorophores disclosed herein is not inherently calcium sensitive, attaching the calcium binding protein domains to the ligand binding protein domain makes such fluorophores calcium sensitive. More specifically, in some embodiments, after binding of the dye-ligand to the ligand binding protein domain, calcium binding to the calcium binding protein domains reversibly changes the fluorescence output of the dye in the attached dye-ligand conjugate.

The hybrid protein-small molecule chemigenetic calcium indicators according to one or more of the embodiments disclosed herein combine the advantages of genetic targetability of proteins with the superior photophysical properties of simple synthetic fluorophores that can be easily delivered to cells. In some embodiments, the calcium indicators disclosed herein provide increased brightness, photostability, and/or spectral range as compared to existing fluorescent proteins. As will be understood by those of ordinary skill in the art, the dyes, ligands, calcium binding protein domains, and capture proteins discussed above are for illustration only and are not intended to limit the scope of the instant disclosure. Accordingly, calcium indicators including any suitable dye, ligand, calcium binding protein domain, and/or capture protein substitute are expressly contemplated herein.

The presently-disclosed subject matter also includes methods of using the calcium indicators. In some embodiments, the methods include measuring changes in calcium levels. For example, in one embodiment, the method includes administering the calcium indicators and measuring changes in fluorescence of the dye by any suitable method. In another embodiment, the changes in fluorescence may be measured through any suitable method such as, but not limited to, observation with a microscope, image capture, video recording, or a combination thereof. In a further embodiment, the changes in fluorescence of the dye may be used to image and/or measure the activity of neurons in live organisms.

The presently-disclosed subject matter is further illustrated by the following specific but non-limiting examples.

The following examples may include compilations of data that are representative of data gathered at various times during the course of development and experimentation related to the presently-disclosed subject matter.

EXAMPLES

Example 1

Figure 4:
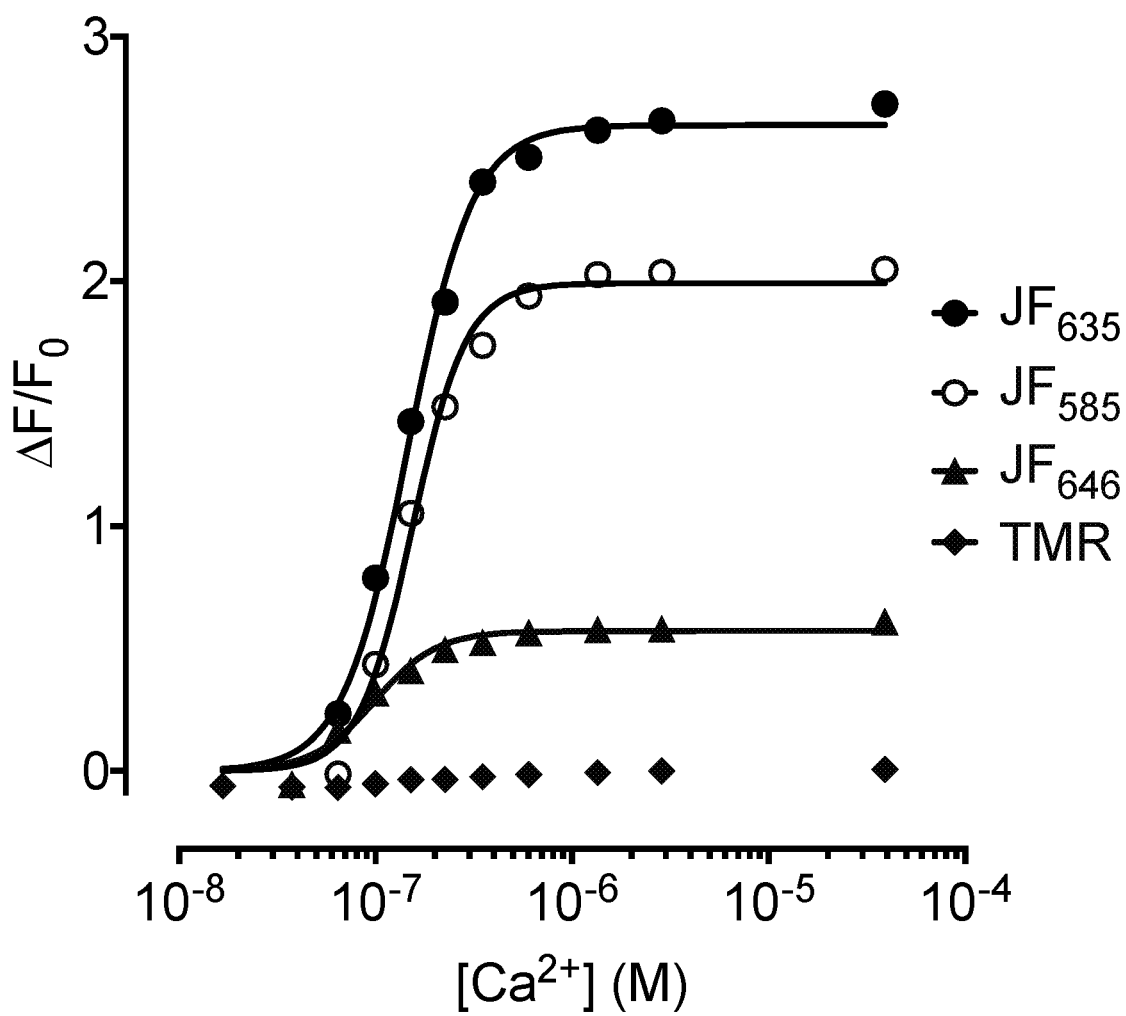
FIG. 4 shows a graph illustrating calcium titrations of chemigenetic calcium indicator protein with $JF_{585}$-HaloTag, $JF_{635}$-HaloTag, $JF_{646}$-HaloTag, and (TMR)-HaloTag dye-ligands bound.
Figure 5A:
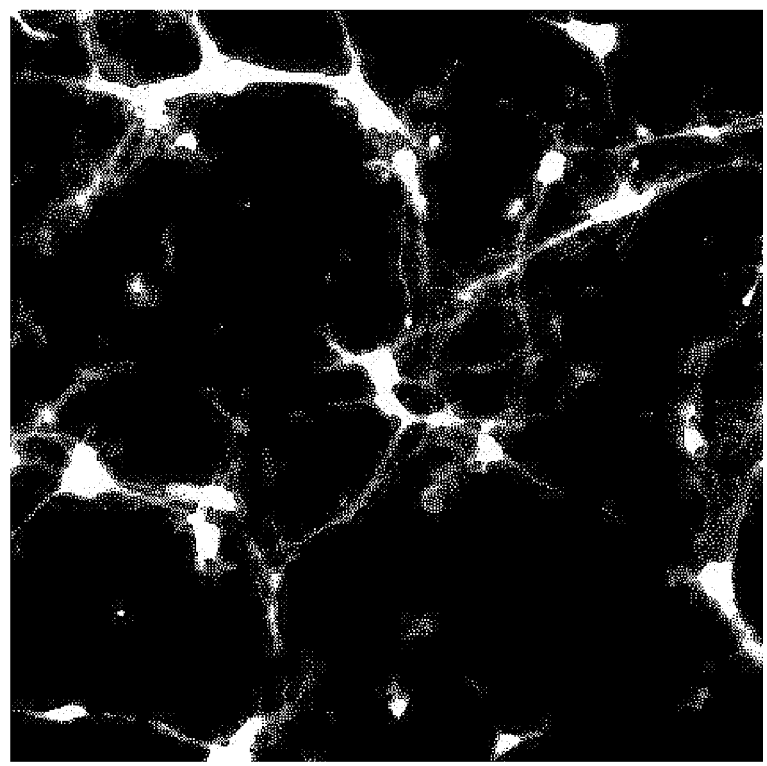
FIGS. 5A-B show graphs and images illustrating fluorescence of rat hippocampal neurons expressing chemigenetic calcium indicator labeled with $JF_{635}$-HaloTag ligand. (A) Fluorescence image of rat hippocampal neurons in culture expressing chemigenetic calcium indicator and labeled with $JF_{635}$-HaloTag ligand. (B) Fluorescence from neurons in (A) in response to action potentials. Action potentials were induced in the neurons with a field electrode during fluorescence imaging. Numbers of action potentials induced appear above each corresponding response in the fluorescence trace (B).
Figure 5B:
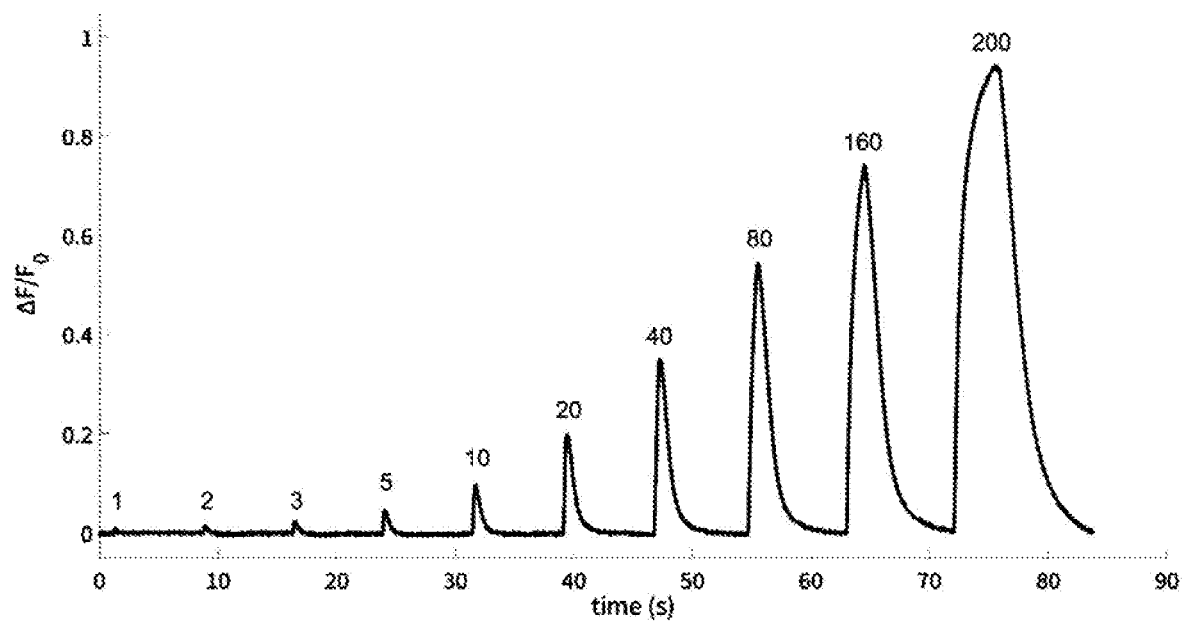

This example describes the formation of a chemigenetic calcium indicator according to an embodiment of the instant disclosure. The chemigenetic calcium indicator was produced by placing the coding sequence of circularly permuted HaloTag between the calcium binding protein calmodulin and a calmodulin binding peptide (SEQ ID NOs: 1 and 2) (FIG. 2). Incubation of the protein with a fluorescent dye/chloroalkane HaloTag ligand conjugate (FIGS. 3D-G) led to covalent attachment of the fluorescent dye to the protein (FIG. 1). Calcium binding then reversibly changed the fluorescence output of the attached fluorescent dye in both purified protein measurements (FIG. 4) and in rat hippocampal neurons in culture stimulated with a field electrode (FIGS. 5A-B).

Example 2

Figure 6:
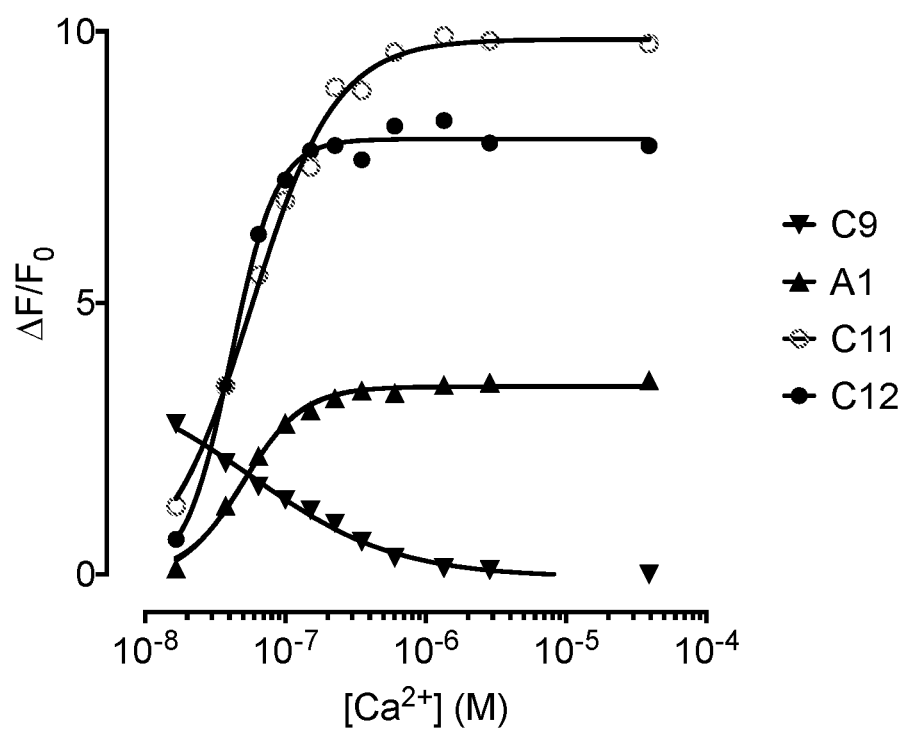
FIG. 6 shows a graph illustrating calcium titrations of chemigenetic calcium indicator proteins bound to $JF_{635}$-HaloTag ligand.

This example compares the fluorescence response of various chemigenetic calcium indicator proteins, including Sv1 (SEQ ID NOs: 3 and 4), A1 (SEQ ID NOs: 5 and 6), C9 (SEQ ID NOs: 7 and 8), C11 (SEQ ID NOs: 9 and 10), and C12 (SEQ ID NOs: 11 and 12), bound to $JF_{635}$-HaloTag ligand. FIG. 6 shows the fluorescence response of the calcium sensor proteins to calcium binding. Table 1 below shows parameters extracted from fits to calcium titrations of chemigenetic calcium indicator proteins bound to $JF_{635}$-HaloTag ligand.

TABLE 1

| Variant | $(\Delta F/F_0)_{max}$ | $K_d$ (nM) | Hill coefficient |
|---|---|---|---|
| Sv1 | 2.6 | 146 | 2.6 |
| A1 | 3.5 | 52 | 2.1 |
| C9 | −3.6 | 58 | 0.9 |
| C11 | 9.9 | 58 | 1.5 |
| C12 | 8.0 | 41 | 2.7 |

As shown in this example, the chemigenetic calcium indicator protein variants have quite different fluorescence responses to binding calcium.

Example 3

Figure 7A:
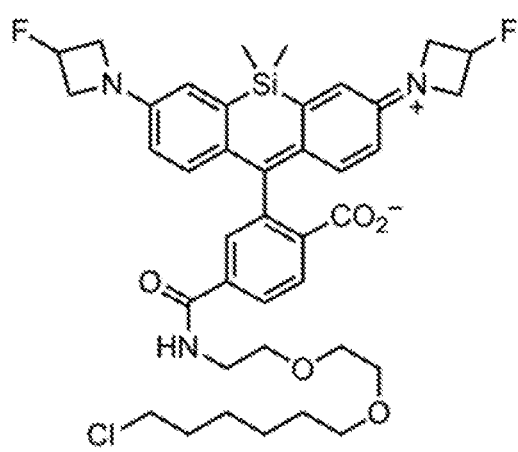
FIGS. 7A-D show graphs and images illustrating various JF-HaloTag ligands and florescence change thereof upon binding calcium. (A) Structure of $JF_{635}$-HaloTag ligand. (B) Derivatives of the azetidine moiety of $JF_{635}$. (C) Fluorescence brightness of $JF_{635}$ derivatives bound to chemigenetic calcium indicator with and without calcium. (D) Magnitude of fluorescence change ($\Delta F/F_0$) of chemigenetic calcium indicator bound to $JF_{635}$ derivatives upon binding calcium.
Figure 7B:
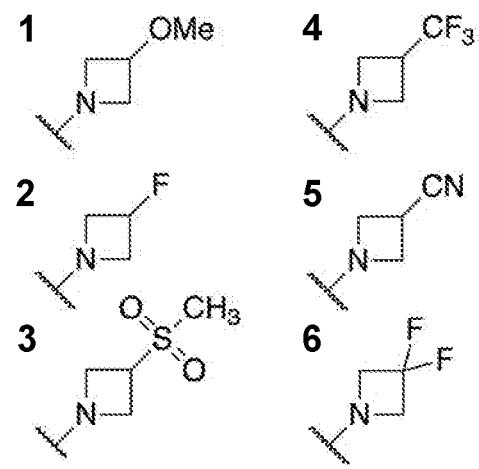

This example describes the formation of various JF-HaloTag ligands and compares the florescence change of calcium indicators including these ligands upon binding calcium. The structure of a $JF_{635}$-HaloTag ligand is shown in FIG. 7A. Through chemical derivatization of the azetidine moiety of $JF_{635}$, the $JF_{635}$-HaloTag ligand derivatives shown in FIG. 7B were produced. Below are $^1$H NMR and FIRMS characterizations for these $JF_{635}$-HaloTag ligand derivatives:

1: $^1$H NMR (400 MHz, $CDCl_3$) δ 7.98 (d, J=8.0 Hz, 1H), 7.91 (dd, J=7.9, 1.4 Hz, 1H), 7.69 (s, 1H), 6.84 (s, 1H), 6.76 (d, J=8.7 Hz, 2H), 6.68 (d, J=2.7 Hz, 2H), 6.28 (dd, J=8.7, 2.6 Hz, 2H), 4.35-4.30 (m, 2H), 4.21-4.08 (m, 4H), 3.75-3.72 (m, 4H), 3.66-3.59 (m, 6H), 3.55-3.53 (m, 2H), 3.50 (t, J=6.7 Hz, 2H), 3.38 (t, J=6.7 Hz, 2H), 3.32 (s, 6H), 1.72 (p, J=6.8 Hz, 2H), 1.50 (p, J=6.9 Hz, 2H), 1.45-1.34 (m, 2H), 1.34-1.23 (m, 2H), 0.64 (s, 3H), 0.57 (s, 3H). HRMS (ESI) calculated for $C_{41}H_{53}ClN_3O_7Si$ $[M+H]^+$ 762.3341, found 762.3352.

2: $JF_{635}$-HaloTag ligand (published)

3: $^1$H NMR (400 MHz, $CDCl_3$) δ 7.96 (d, J=8.0 Hz, 1H), 7.89 (dd, J=8.0, 1.4 Hz, 1H), 7.67 (d, J=1.3 Hz, 1H), 6.94 (br s, 1H), 6.82 (d, J=8.7 Hz, 2H), 6.69 (d, J=2.6 Hz, 2H), 6.30 (dd, J=8.7, 2.7 Hz, 2H), 4.24-4.18 (m, 8H), 4.16-4.04 (m, 2H), 3.68-3.59 (m, 6H), 3.56-3.54 (m, 2H), 3.49 (t, J=6.6 Hz, 2H), 3.39 (t, J=6.7 Hz, 2H), 2.95 (s, 6H), 1.76-1.66 (m, 2H), 1.51 (p, J=6.9 Hz, 2H), 1.42-1.35 (m, 2H), 1.33-1.22 (m, 2H), 0.64 (s, 3H), 0.56 (s, 3H). HRMS (ESI) calculated for $C_{41}H_{53}ClN_3O_9S_2Si$ $[M+H]^+$ 858.2681, found 858.2690.

4: $^1$H NMR (400 MHz, $CDCl_3$) δ 8.03-7.97 (m, 1H), 7.90 (dd, J=8.0, 1.4 Hz, 1H), 7.70 (s, 1H), 6.86-6.79 (m, 3H), 6.67 (d, J=2.7 Hz, 2H), 6.29 (dd, J=8.7, 2.7 Hz, 2H), 4.09-4.05 (m, 4H), 3.99-3.94 (m, 4H), 3.66-3.60 (m, 6H), 3.58-3.54 (m, 2H), 3.50 (t, J=6.6 Hz, 2H), 3.42-3.38 (m, 4H), 1.79-1.65 (m, 2H), 1.52 (p, J=6.9 Hz, 2H), 1.45-1.36 (m, 2H), 1.36-1.19 (m, 2H), 0.65 (s, 3H), 0.58 (s, 3H). HRMS (ESI) calculated for $C_{41}H_{47}ClF_6N_3O_5Si$ $[M+H]^+$ 838.2878, found 838.2891.

5: $^1$H NMR (400 MHz, $CDCl_3$) δ 7.98 (dd, J=8.0, 0.7 Hz, 1H), 7.88 (dd, J=8.0, 1.4 Hz, 1H), 7.70 (s, 1H), 6.84 (d, J=8.7 Hz, 3H), 6.67 (d, J=2.7 Hz, 2H), 6.30 (dd, J=8.7, 2.7 Hz, 2H), 4.22-4.18 (m, 4H), 4.11-4.08 (m, 4H), 3.68-3.54 (m, 10H), 3.50 (t, J=6.6 Hz, 2H), 3.41 (t, J=6.7 Hz, 2H), 1.79-1.67 (m, 2H), 1.52 (p, J=6.9 Hz, 2H), 1.45-1.36 (m, 2H), 1.34-1.21 (m, 2H), 0.66 (s, 3H), 0.58 (s, 3H). HRMS (ESI) calculated for $C_{41}H_{47}ClN_5O_5Si$ $[M+H]^+$ 752.3035, found 752.3044.

6: $^1$H NMR (400 MHz, $CDCl_3$) δ 7.99 (d, J=7.9 Hz, 1H), 7.89 (dd, J=8.0, 1.4 Hz, 1H), 7.71 (d, J=1.2 Hz, 1H), 6.87-6.83 (m, 3H), 6.72 (d, J=2.7 Hz, 2H), 6.35 (dd, J=8.7, 2.7 Hz, 2H), 4.23 (t, J=11.7 Hz, 8H), 3.67-3.59 (m, 6H), 3.56-3.54 (m, 2H), 3.50 (t, J=6.6 Hz, 2H), 3.40 (t, J=6.7 Hz, 2H), 1.77-1.68 (m, 2H), 1.57-1.48 (m, 2H), 1.46-1.36 (m, 2H), 1.35-1.22 (m, 2H), 0.67 (s, 3H), 0.59 (s, 3H). HRMS (ESI) calculated for $C_{39}H_{45}ClF_4N_3O_5Si$ $[M+H]^+$ 774.2753, found 774.2759.

Figure 7C:
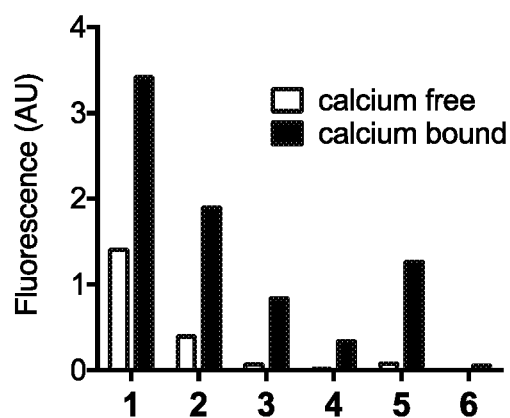
Figure 7D:
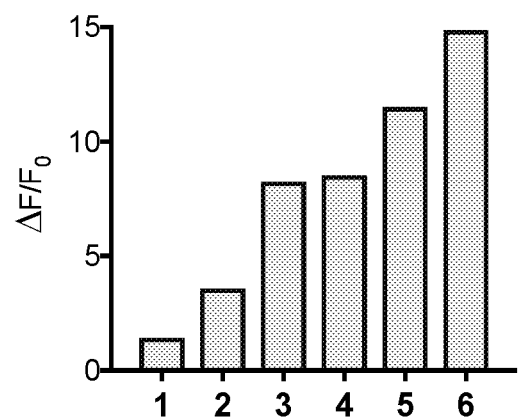

After characterizing these derivatives, the fluorescence brightness thereof was measured when bound to a chemigenetic calcium indicator with and without calcium (FIG. 7C). Additionally, the magnitude of fluorescence change $(\Delta F/F_0)$ of the chemigenetic calcium indicator bound to these $JF_{635}$ derivatives was measured upon binding calcium (FIG. 7D). As shown in FIGS. 7C-D, these derivatives formed calcium indicators with variable brightness and fluorescence change when bound to the sensor protein.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lin, M. Z. and M. J. Schnitzer, *Genetically encoded indicators of neuronal activity*. Nat Neurosci, 2016. 19(9): p. 1142-53.
2. Grimm, J. B., et al., *A general method to improve fluorophores for live-cell and single-molecule microscopy*. Nat Methods, 2015. 12(3): p. 244-50, 3 p following 250.

3. Grimm, J. B., et al., *A general method to fine-tune fluorophores for live-cell and in vivo imaging.* Nat Methods, 2017. 14(10): p. 987-994.
4. Los, G. V., et al., *HaloTag: a novel protein labeling technology for cell imaging and protein analysis.* ACS Chem Biol, 2008. 3(6): p. 373-82.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A chemigenetic calcium indicator, comprising:
   (a) a calcium-binding protein domain,
   (b) a ligand-binding protein domain attached to the calcium-binding protein domain, and
   (c) a fluorescent dye conjugated to a ligand for the ligand-binding protein domain;
   wherein the calcium indicator comprises a polypeptide selected from the group consisting of SEQ ID NO: 2, 4, 6, 8, 10, and 12.

2. The chemigenetic calcium indicator of claim 1, wherein the ligand binding protein domain is a self-labeling protein.

3. The chemigenetic calcium indicator of claim 1, wherein the ligand binding protein domain comprises a non-covalent capture protein.

4. The chemigenetic calcium indicator of claim 3, wherein the non-covalent capture protein is selected from the group consisting of a self-labeling protein, a biotin-avidin, and a combination thereof.

5. The chemigenetic calcium indicator of claim 1, wherein the calcium binding protein domain comprises calmodulin and a calmodulin binding peptide.

6. The chemigenetic calcium indicator of claim 1, wherein the calcium indicator comprises a polypeptide consisting of SEQ ID NO: 2.

7. The chemigenetic calcium indicator of claim 1, wherein the calcium indicator comprises a polypeptide consisting of SEQ ID NO: 4.

8. The chemigenetic calcium indicator of claim 1, wherein the calcium indicator comprises a polypeptide consisting of SEQ ID NO: 6.

9. The chemigenetic calcium indicator of claim 1, wherein the calcium indicator comprises a polypeptide consisting of SEQ ID NO: 8.

10. The chemigenetic calcium indicator of claim 1, wherein the calcium indicator comprises a polypeptide consisting of SEQ ID NO: 10.

11. The chemigenetic calcium indicator of claim 1, wherein the calcium indicator comprises a polypeptide consisting of SEQ ID NO: 12.

12. The chemigenetic calcium indicator of claim 1, wherein the fluorescent dye is selected from the group consisting of azetidine-containing dyes and rhodamines.

13. A method of measuring calcium, the method comprising administering the chemigenetic calcium indicator of claim 1 and determining changes in fluorescence.

14. The method of claim 13, wherein the ligand binding protein comprises a self-labeling protein and the fluorescent dye conjugated to the ligand comprises a ligand for the self-labeling protein conjugated to the fluorescent dye.

* * * * *

SEQUENCE LISTING

```
<160> NUMBER OF SEQ ID NOS: 13

<210> SEQ ID NO 1
<211> LENGTH: 1548
<212> TYPE: DNA
<213> ORGANISM: Artificial
<220> FEATURE:
<223> OTHER INFORMATION: Synthetic chemigenetic calcium indicator

<400> SEQUENCE: 1
atgctgcaga acgagcttgc tcttaagttg gctggacttg atattaacaa gactggaggt      60
tctcatcatc accaccacca tggatccgcc cgtcgtaaat ggcagaaaac aggccatgcg     120
gttcgtgcta tcggtcgttt gtcgagccca gaatttgccc gcgagacctt ccaggccttc     180
cgcaccaccg acgtcggccg caagctgatc atcgatcaga acgtttttat cgagggtacg     240
ctgccgatgg gtgtcgtccg cccgctgact gaagtcgaga tggaccatta ccgcgagccg     300
ttcctgaatc ctgttgaccg cgagccactg tggcgcttcc caaacgagct gccaatcgcc     360
ggtgagccag cgaacatcgt cgcgctggtc gaagaataca tggactggct gcaccagtcc     420
cctgtcccga agctgctgtt ctggggcacc ccaggcgttc tgatcccacc ggccgaagcc     480
gctcgcctgg ccaaaagcct gcctaactgc aaggctgtgg acatcggccc gggtctgaat     540
ctgctgcaag aagacaaccc ggacctgatc ggcagcgaga tcgcgcgctg gctgtcgacg     600
ctcgagattt ccggcggagg aacaggtggt tctggtggaa caggggggtag cggaggtaca     660 ggaggaagta tggcagaaat cggtactggc tttccattcg accccatta tgtggaagtc      720 ctgggcgagc gcatgcacta cgtcgatgtt ggtccgcgcg atggcacccc tgtgctgttc     780
ctgcacggta cccgacctc ctcctacgtg tggcgcaaca tcatcccgca tgttgcaccg     840
acccatcgct gcattgctcc agacctgatc ggtatgggca atccgacaa accagacctg      900 ggttatttct tcgacgacca cgtccgcttc atggatgcct tcatcgaagc cctggtctg     960 gaagaggtcg tcctggtcat tcacgactgg ggctccgctc tgggtttcca ctgggccaag    1020
cgcaatccag agcgcgtcaa aggtattgca tttatggagt tcatccgccc tatcccgacc    1080
tgggacgaat ggccggagtt cgcgcgtgat caattaacag aggaacagat tgcggagttt    1140
aaggaagcgt tctctttat tgataaggat ggcgacggta caatcactac taaagaattg    1200
ggaacagtca tgcgctcatt ggggcaaaat ccgacagagg ctgaattgca ggacatgatt    1260
aacgaggtag acgccgatgg gaacgggact atcgactttc cggaatttct tactatgatg    1320
gcacgcaaaa tgaaagatac cgattctgaa gaagagatcc gtgaagcttt ccgtgttttt    1380
gataaagatg gaaacggcta catcagtgct gctgagttac gccatgtgat gacaaatctg    1440
ggggaaaaac ttaccgacga agaagtagac gaaatgattc gcgaggcgga tattgacggg    1500
gatggacaag taaactacga ggaatttgtg cagatgatga ccgccaag              1548

<210> SEQ ID NO 2
<211> LENGTH: 516
<212> TYPE: PRT
<213> ORGANISM: Artificial
<220> FEATURE:
<223> OTHER INFORMATION: Synthetic chemigenetic calcium indicator
```

<400> SEQUENCE: 2

```
Met Leu Gln Asn Glu Leu Ala Leu Lys Leu Ala Gly Leu Asp Ile Asn
1               5                   10                  15

Lys Thr Gly Gly Ser His His His His His Gly Ser Ala Arg Arg
            20                  25                  30

Lys Trp Gln Lys Thr Gly His Ala Val Arg Ala Ile Gly Arg Leu Ser
            35                  40                  45

Ser Pro Glu Phe Ala Arg Glu Thr Phe Gln Ala Phe Arg Thr Thr Asp
        50                  55                  60

Val Gly Arg Lys Leu Ile Ile Asp Gln Asn Val Phe Ile Glu Gly Thr
65                  70                  75                  80

Leu Pro Met Gly Val Val Arg Pro Leu Thr Glu Val Glu Met Asp His
                85                  90                  95

Tyr Arg Glu Pro Phe Leu Asn Pro Val Asp Arg Glu Pro Leu Trp Arg
            100                 105                 110

Phe Pro Asn Glu Leu Pro Ile Ala Gly Glu Pro Ala Asn Ile Val Ala
        115                 120                 125

Leu Val Glu Glu Tyr Met Asp Trp Leu His Gln Ser Pro Val Pro Lys
130                 135                 140

Leu Leu Phe Trp Gly Thr Pro Gly Val Leu Ile Pro Pro Ala Glu Ala
145                 150                 155                 160

Ala Arg Leu Ala Lys Ser Leu Pro Asn Cys Lys Ala Val Asp Ile Gly
                165                 170                 175

Pro Gly Leu Asn Leu Leu Gln Glu Asp Asn Pro Asp Leu Ile Gly Ser
            180                 185                 190

Glu Ile Ala Arg Trp Leu Ser Thr Leu Glu Ile Ser Gly Gly Gly Thr
        195                 200                 205

Gly Gly Ser Gly Gly Thr Gly Gly Ser Gly Gly Thr Gly Gly Ser Met
210                 215                 220

Ala Glu Ile Gly Thr Gly Phe Pro Phe Asp Pro His Tyr Val Glu Val
225                 230                 235                 240

Leu Gly Glu Arg Met His Tyr Val Asp Val Gly Pro Arg Asp Gly Thr
                245                 250                 255

Pro Val Leu Phe Leu His Gly Asn Pro Thr Ser Ser Tyr Val Trp Arg
            260                 265                 270

Asn Ile Ile Pro His Val Ala Pro Thr His Arg Cys Ile Ala Pro Asp
        275                 280                 285

Leu Ile Gly Met Gly Lys Ser Asp Lys Pro Asp Leu Gly Tyr Phe Phe
290                 295                 300

Asp Asp His Val Arg Phe Met Asp Ala Phe Ile Glu Ala Leu Gly Leu
305                 310                 315                 320

Glu Glu Val Val Leu Val Ile His Asp Trp Gly Ser Ala Leu Gly Phe
                325                 330                 335

His Trp Ala Lys Arg Asn Pro Glu Arg Val Lys Gly Ile Ala Phe Met
            340                 345                 350

Glu Phe Ile Arg Pro Ile Pro Thr Trp Asp Glu Trp Pro Glu Phe Ala
        355                 360                 365

Arg Asp Gln Leu Thr Glu Glu Gln Ile Ala Glu Phe Lys Glu Ala Phe
    370                 375                 380

Ser Leu Phe Asp Lys Asp Gly Asp Gly Thr Ile Thr Thr Lys Glu Leu
385                 390                 395                 400

Gly Thr Val Met Arg Ser Leu Gly Gln Asn Pro Thr Glu Ala Glu Leu
```

```
                        405                 410                 415
Gln Asp Met Ile Asn Glu Val Asp Ala Asp Gly Asn Gly Thr Ile Asp
                420                 425                 430

Phe Pro Glu Phe Leu Thr Met Met Ala Arg Lys Met Lys Asp Thr Asp
            435                 440                 445

Ser Glu Glu Ile Arg Glu Ala Phe Arg Val Phe Asp Lys Asp Gly
        450                 455                 460

Asn Gly Tyr Ile Ser Ala Ala Glu Leu Arg His Val Met Thr Asn Leu
465                 470                 475                 480

Gly Glu Lys Leu Thr Asp Glu Glu Val Asp Glu Met Ile Arg Glu Ala
                485                 490                 495

Asp Ile Asp Gly Asp Gly Gln Val Asn Tyr Glu Glu Phe Val Gln Met
            500                 505                 510

Met Thr Ala Lys
        515

<210> SEQ ID NO 3
<211> LENGTH: 1461
<212> TYPE: DNA
<213> ORGANISM: Artificial
<220> FEATURE:
<223> OTHER INFORMATION: Synthetic chemigenetic calcium indicator

<400> SEQUENCE: 3
gcccgtcgta aatggcagaa acaggccat gcggttcgtg ctatcggtcg tttgtcgagc      60
ccagaatttg cccgcgagac cttccaggcc ttccgcacca ccgacgtcgg ccgcaagctg    120
atcatcgatc agaacgtttt tatcgagggt acgctgccga tgggtgtcgt ccgcccgctg    180
actgaagtcg agatggacca ttaccgcgag ccgttcctga atcctgttga ccgcgagcca    240
ctgtggcgct tcccaaacga gctgccaatc gccggtgagc cagcgaacat cgtcgcgctg    300
gtcgaagaat acatggactg gctgcaccag tcccctgtcc cgaagctgct gttctggggc    360
accccaggcg ttctgatccc accggccgaa gccgctcgcc tggccaaaag cctgcctaac    420
tgcaaggctg tggacatcgg cccgggtctg aatctgctgc aagaagacaa cccggacctg    480
atcggcagcg agatcgcgcg ctggctgtcg acgctcgaga tttccggcgg aggaacaggt    540
ggttctggtg aacaggggg tagcggaggt acaggaggaa gtatggcaga aatcggtact    600
ggctttccat cgacccca ttatgtgaa gtcctgggcg agcgcatgca ctacgtcgat    660
gttggtccgc gcgatggcac ccctgtgctg ttcctgcacg gtaacccgac ctcctcctac    720
gtgtggcgca acatcatccc gcatgttgca ccgacccatc gctgcattgc tccagacctg    780
atcggtatgg gcaaatccga caaaccagac ctgggttatt tcttcgacga ccacgtccgc    840
ttcatggatg ccttcatcga agccctgggt ctggaagagg tcgtcctggt cattcacgac    900
tggggctccg ctctgggttt ccactgggcc aagcgcaatc agagcgcgt caaaggtatt    960 gcatttatgg agttcatccg ccctatcccg acctgggacg aatggccgga gttcgcgcgt    1020
gatcaattaa cagaggaaca gattgcggag tttaaggaag cgttctcttt atttgataag    1080
gatggcgacg gtacaatcac tactaaagaa ttgggaacag tcatgcgctc attggggcaa    1140
aatccgacag aggctgaatt gcaggacatg attaacgagg tagacgccga tgggaacggg    1200
actatcgact tccggaatt tcttactatg atggcacgca aaatgaaaga taccgattct    1260
gaagaagaga tccgtgaagc ttttcgtgtt tttgataaag atgggaacgg ctacatcagt    1320
gctgctgagt tacgccatgt gatgacaaat ctgggggaaa aacttaccga cgaagaagta    1380
```

```
gacgaaatga ttcgcgaggc ggatattgac ggggatggac aagtaaacta cgaggaattt    1440
gtgcagatga tgaccgccaa g                                              1461
```

<210> SEQ ID NO 4
<211> LENGTH: 487
<212> TYPE: PRT
<213> ORGANISM: Artificial
<220> FEATURE:
<223> OTHER INFORMATION: Synthetic chemigenetic calcium indicator

<400> SEQUENCE: 4

```
Ala Arg Arg Lys Trp Gln Lys Thr Gly His Ala Val Arg Ala Ile Gly
1               5                   10                  15

Arg Leu Ser Ser Pro Glu Phe Ala Arg Glu Thr Phe Gln Ala Phe Arg
            20                  25                  30

Thr Thr Asp Val Gly Arg Lys Leu Ile Ile Asp Gln Asn Val Phe Ile
        35                  40                  45

Glu Gly Thr Leu Pro Met Gly Val Val Arg Pro Leu Thr Glu Val Glu
    50                  55                  60

Met Asp His Tyr Arg Glu Pro Phe Leu Asn Pro Val Asp Arg Glu Pro
65                  70                  75                  80

Leu Trp Arg Phe Pro Asn Glu Leu Pro Ile Ala Gly Glu Pro Ala Asn
                85                  90                  95

Ile Val Ala Leu Val Glu Glu Tyr Met Asp Trp Leu His Gln Ser Pro
            100                 105                 110

Val Pro Lys Leu Leu Phe Trp Gly Thr Pro Gly Val Leu Ile Pro Pro
        115                 120                 125

Ala Glu Ala Ala Arg Leu Ala Lys Ser Leu Pro Asn Cys Lys Ala Val
    130                 135                 140

Asp Ile Gly Pro Gly Leu Asn Leu Leu Gln Glu Asp Asn Pro Asp Leu
145                 150                 155                 160

Ile Gly Ser Glu Ile Ala Arg Trp Leu Ser Thr Leu Glu Ile Ser Gly
                165                 170                 175

Gly Gly Thr Gly Gly Ser Gly Gly Thr Gly Gly Ser Gly Gly Thr Gly
            180                 185                 190

Gly Ser Met Ala Glu Ile Gly Thr Gly Phe Pro Phe Asp Pro His Tyr
        195                 200                 205

Val Glu Val Leu Gly Glu Arg Met His Tyr Val Asp Val Gly Pro Arg
    210                 215                 220

Asp Gly Thr Pro Val Leu Phe Leu His Gly Asn Pro Thr Ser Ser Tyr
225                 230                 235                 240

Val Trp Arg Asn Ile Ile Pro His Val Ala Pro Thr His Arg Cys Ile
                245                 250                 255

Ala Pro Asp Leu Ile Gly Met Gly Lys Ser Asp Lys Pro Asp Leu Gly
            260                 265                 270

Tyr Phe Phe Asp Asp His Val Arg Phe Met Asp Ala Phe Ile Glu Ala
        275                 280                 285

Leu Gly Leu Glu Glu Val Val Leu Val Ile His Asp Trp Gly Ser Ala
    290                 295                 300

Leu Gly Phe His Trp Ala Lys Arg Asn Pro Glu Arg Val Lys Gly Ile
305                 310                 315                 320

Ala Phe Met Glu Phe Ile Arg Pro Ile Pro Thr Trp Asp Glu Trp Pro
                325                 330                 335

Glu Phe Ala Arg Asp Gln Leu Thr Glu Glu Gln Ile Ala Glu Phe Lys
            340                 345                 350
```

Glu Ala Phe Ser Leu Phe Asp Lys Asp Gly Asp Gly Thr Ile Thr Thr
    355                 360                 365

Lys Glu Leu Gly Thr Val Met Arg Ser Leu Gly Gln Asn Pro Thr Glu
    370                 375                 380

Ala Glu Leu Gln Asp Met Ile Asn Glu Val Asp Ala Asp Gly Asn Gly
385                 390                 395                 400

Thr Ile Asp Phe Pro Glu Phe Leu Thr Met Met Ala Arg Lys Met Lys
                405                 410                 415

Asp Thr Asp Ser Glu Glu Glu Ile Arg Glu Ala Phe Arg Val Phe Asp
                420                 425                 430

Lys Asp Gly Asn Gly Tyr Ile Ser Ala Ala Glu Leu Arg His Val Met
    435                 440                 445

Thr Asn Leu Gly Glu Lys Leu Thr Asp Glu Glu Val Asp Glu Met Ile
    450                 455                 460

Arg Glu Ala Asp Ile Asp Gly Asp Gly Gln Val Asn Tyr Glu Glu Phe
465                 470                 475                 480

Val Gln Met Met Thr Ala Lys
                485

<210> SEQ ID NO 5
<211> LENGTH: 1461
<212> TYPE: DNA
<213> ORGANISM: Artificial
<220> FEATURE:
<223> OTHER INFORMATION: Synthetic chemigenetic calcium indicator

<400> SEQUENCE: 5
gcccgtcgta aatggcagaa acaggccat gcggttcgtg ctatcggtcg tttgtcgagc      60
cctgagtttg cagcggagac cttccaggcc ttccgcacca ccgacgtcgg ccgcaagctg     120
atcatcgatc agaacgtttt tatcgagggt acgctgccga tgggtgtcgt ccgcccgctg     180
actgaagtcg agatggacca ttaccgcgag ccgttcctga tcctgttga ccgcgagcca      240 ctgtggcgct tcccaaacga gctgccaatc gccggtgagc cagcgaacat cgtcgcgctg     300
gtcgaagaat acatggactg gctgcaccag tcccctgtcc cgaagctgct gttctggggc     360
accccaggcg ttctgatccc accggccgaa gccgctcgcc tggccaaaag cctgcctaac     420
tgcaaggctg tggacatcgg cccgggtctg aatctgctgc aagaagacaa cccggacctg     480
atcggcagcg agatcgcgcg ctggctgtcg acgctcgaga tttccggcgg aggaacaggt     540
ggttctggtg gaacagggg tagcggaggt acaggaggaa gtatgcgga gatcggaact      600 ggattcccgt tgatccgca ttatgtggaa gttctgggag agcgcatgca ttatgtggac      660
gttggtcctc gtgatgggac accagtgctg ttccttcacg gcaatccgac atcgtcgtac     720
gtgtggcgta atatcatccc gcacgttgcc cccacgcacc gctgcattgc ccctgactta     780
attggtatgg ggaaaagtga taagcctgat ctggggtact ctttgacga ccacgtacgc      840 ttcatggatg ctttttattga agcattgggt ttggaggaag tagttttggt gatccatgat     900
tggggtagtg ctctggggtt ccattgggcc aagcgtaacc agaacgcgt gaaaggaatt      960 gcctttatgg agttcatccg tccgattcca acatgggacg aatggcgaga atttgcacgc    1020
gatcaattaa cagaggaaca gattgcggag tttaaggaag cgttctcttt atttgataag    1080
gatggcgacg gtacaatcac tactaaagaa ttgggaacag tcatgcgctc attggggcaa    1140
aatccgacag aggctgaatt gcaggacatg attaacgagg tagacgccga tgggaacggg    1200
actatcgact ttccggaatt tcttactatg atggcacgca aaatgaaaga taccgattct    1260

```
gaagaagaga tccgtgaagc tttccgtgtt tttgataaag atgggaacgg ctacatcagt   1320
gctgctgagt tacgccatgt gatgacaaat ctgggggaaa aacttaccga cgaagaagta   1380
gacgaaatga ttcgcgaggc ggatattgac ggggatggac aagtaaacta cgaggaattt   1440
gtgcagatga tgaccgccaa g                                             1461

<210> SEQ ID NO 6
<211> LENGTH: 487
<212> TYPE: PRT
<213> ORGANISM: Artificial
<220> FEATURE:
<223> OTHER INFORMATION: Synthetic chemigenetic calcium indicator

<400> SEQUENCE: 6
```

Ala Arg Arg Lys Trp Gln Lys Thr Gly His Ala Val Arg Ala Ile Gly
1               5                   10                  15

Arg Leu Ser Ser Pro Glu Phe Ala Ala Glu Thr Phe Gln Ala Phe Arg
                20                  25                  30

Thr Thr Asp Val Gly Arg Lys Leu Ile Ile Asp Gln Asn Val Phe Ile
                35                  40                  45

Glu Gly Thr Leu Pro Met Gly Val Val Arg Pro Leu Thr Glu Val Glu
50                  55                  60

Met Asp His Tyr Arg Glu Pro Phe Leu Asn Pro Val Asp Arg Glu Pro
65                  70                  75                  80

Leu Trp Arg Phe Pro Asn Glu Leu Pro Ile Ala Gly Glu Pro Ala Asn
                85                  90                  95

Ile Val Ala Leu Val Glu Glu Tyr Met Asp Trp Leu His Gln Ser Pro
                100                 105                 110

Val Pro Lys Leu Leu Phe Trp Gly Thr Pro Gly Val Leu Ile Pro Pro
                115                 120                 125

Ala Glu Ala Ala Arg Leu Ala Lys Ser Leu Pro Asn Cys Lys Ala Val
            130                 135                 140

Asp Ile Gly Pro Gly Leu Asn Leu Leu Gln Glu Asp Asn Pro Asp Leu
145                 150                 155                 160

Ile Gly Ser Glu Ile Ala Arg Trp Leu Ser Thr Leu Glu Ile Ser Gly
                165                 170                 175

Gly Gly Thr Gly Gly Ser Gly Gly Thr Gly Gly Ser Gly Gly Thr Gly
                180                 185                 190

Gly Ser Met Ala Glu Ile Gly Thr Gly Phe Pro Phe Asp Pro His Tyr
            195                 200                 205

Val Glu Val Leu Gly Glu Arg Met His Tyr Val Asp Val Gly Pro Arg
                210                 215                 220

Asp Gly Thr Pro Val Leu Phe Leu His Gly Asn Pro Thr Ser Ser Tyr
225                 230                 235                 240

Val Trp Arg Asn Ile Ile Pro His Val Ala Pro Thr His Arg Cys Ile
                245                 250                 255

Ala Pro Asp Leu Ile Gly Met Gly Lys Ser Asp Lys Pro Asp Leu Gly
                260                 265                 270

Tyr Phe Phe Asp Asp His Val Arg Phe Met Asp Ala Phe Ile Glu Ala
            275                 280                 285

Leu Gly Leu Glu Glu Val Val Leu Val Ile His Asp Trp Gly Ser Ala
            290                 295                 300

Leu Gly Phe His Trp Ala Lys Arg Asn Pro Glu Arg Val Lys Gly Ile
305                 310                 315                 320

```
Ala Phe Met Glu Phe Ile Arg Pro Ile Pro Thr Trp Asp Glu Trp Arg
                325                 330                 335

Glu Phe Ala Arg Asp Gln Leu Thr Glu Glu Gln Ile Ala Glu Phe Lys
            340                 345                 350

Glu Ala Phe Ser Leu Phe Asp Lys Asp Gly Asp Gly Thr Ile Thr Thr
        355                 360                 365

Lys Glu Leu Gly Thr Val Met Arg Ser Leu Gly Gln Asn Pro Thr Glu
    370                 375                 380

Ala Glu Leu Gln Asp Met Ile Asn Glu Val Asp Ala Asp Gly Asn Gly
385                 390                 395                 400

Thr Ile Asp Phe Pro Glu Phe Leu Thr Met Met Ala Arg Lys Met Lys
                405                 410                 415

Asp Thr Asp Ser Glu Glu Glu Ile Arg Glu Ala Phe Arg Val Phe Asp
            420                 425                 430

Lys Asp Gly Asn Gly Tyr Ile Ser Ala Ala Glu Leu Arg His Val Met
        435                 440                 445

Thr Asn Leu Gly Glu Lys Leu Thr Asp Glu Glu Val Asp Glu Met Ile
    450                 455                 460

Arg Glu Ala Asp Ile Asp Gly Asp Gly Gln Val Asn Tyr Glu Glu Phe
465                 470                 475                 480

Val Gln Met Met Thr Ala Lys
                485

<210> SEQ ID NO 7
<211> LENGTH: 1440
<212> TYPE: DNA
<213> ORGANISM: Artificial
<220> FEATURE:
<223> OTHER INFORMATION: Synthetic chemigenetic calcium indicator

<400> SEQUENCE: 7
gcccgtcgta aatggcagaa acaggccat gcggttcgtg ctatcggtcg tttgtcgagc      60
tgggagacct tccaggcctt ccgcaccacc gacgtcggcc gcaagctgat catcgatcag    120
aacgttttta tcgagggtac gctgccgatg ggtgtcgtcc gcccgctgac tgaagtcgag    180
atggaccatt accgcgagcc gttcctgaat cctgttgacc gcgagccact gtggcgcttc    240
ccaaacgagc tgccaatcgc cggtgagcca gcgaacatcg tcgcgctggt cgaagaatac    300
atggactggc tgcaccagtc ccctgtcccg aagctgctgt tctggggcac ccaggcgtt    360 ctgatcccac cggccgaagc cgctcgcctg gccaaaagcc tgcctaactg caaggctgtg    420
gacatcggcc cgggtctgaa tctgctgcaa gaagacaacc cggacctgat cggcagcgag    480
atcgcgcgct ggctgtcgac gctcgagatt ccggcggag aacaggtgg ttctggtgga    540 acaggggta gcgaggtac aggaggaagt atggcggaga tcggaactgg attcccgttt    600
gatccgcatt atgtggaagt tctgggagag cgcatgcatt atgtggacgt tggtcctcgt    660
gatgggacac cagtgctgtt ccttcacggc aatccgacat cgtcgtacgt gtggcgtaat    720
atcatcccgc acgttgcccc cacgcaccgc tgcattgccc ctgacttaat tggtatgggg    780
aaaagtgata agcctgatct ggggtacttc tttgacgacc acgtacgctt catggatgct    840
tttattgaag cattgggttt ggaggaagta gttttggtga tccatgattg ggtagtgct    900 ctggggttcc attgggccaa gcgtaaccca gaacgcgtga aggaattgc ctttatggag    960 ttcatccgtc cgattccaac atgggacgaa tggccccgcg atcaattaac agaggaacag   1020
attgcggagt ttaaggaagc gttctcttta tttgataagg atggcgacgg tacaatcact   1080
```

-continued

```
actaaagaat tgggaacagt catgcgctca ttggggcaaa atccgacaga ggctgaattg    1140
caggacatga ttaacgaggt agacgccgat gggaacggga ctatcgactt tccggaattt    1200
cttactatga tggcacgcaa aatgaaagat accgattctg aagaagagat ccgtgaagct    1260
ttccgtgttt ttgataaaga tgggaacggc tacatcagtg ctgctgagtt acgccatgtg    1320
atgacaaatc tgggggaaaa acttaccgac gaagaagtag acgaaatgat tcgcgaggcg    1380
gatattgacg gggatggaca agtaaactac gaggaatttg tgcagatgat gaccgccaag    1440
```

<210> SEQ ID NO 8
<211> LENGTH: 480
<212> TYPE: PRT
<213> ORGANISM: Artificial
<220> FEATURE:
<223> OTHER INFORMATION: Synthetic chemigenetic calcium indicator

<400> SEQUENCE: 8

```
Ala Arg Arg Lys Trp Gln Lys Thr Gly His Ala Val Arg Ala Ile Gly
 1               5                  10                  15

Arg Leu Ser Ser Trp Glu Thr Phe Gln Ala Phe Arg Thr Thr Asp Val
             20                  25                  30

Gly Arg Lys Leu Ile Ile Asp Gln Asn Val Phe Ile Glu Gly Thr Leu
         35                  40                  45

Pro Met Gly Val Val Arg Pro Leu Thr Glu Val Glu Met Asp His Tyr
     50                  55                  60

Arg Glu Pro Phe Leu Asn Pro Val Asp Arg Glu Pro Leu Trp Arg Phe
 65                  70                  75                  80

Pro Asn Glu Leu Pro Ile Ala Gly Glu Pro Ala Asn Ile Val Ala Leu
                 85                  90                  95

Val Glu Glu Tyr Met Asp Trp Leu His Gln Ser Pro Val Pro Lys Leu
            100                 105                 110

Leu Phe Trp Gly Thr Pro Gly Val Leu Ile Pro Pro Ala Glu Ala Ala
        115                 120                 125

Arg Leu Ala Lys Ser Leu Pro Asn Cys Lys Ala Val Asp Ile Gly Pro
    130                 135                 140

Gly Leu Asn Leu Leu Gln Glu Asp Asn Pro Asp Leu Ile Gly Ser Glu
145                 150                 155                 160

Ile Ala Arg Trp Leu Ser Thr Leu Glu Ile Ser Gly Gly Thr Gly
                165                 170                 175

Gly Ser Gly Gly Thr Gly Gly Ser Gly Gly Thr Gly Ser Met Ala
            180                 185                 190

Glu Ile Gly Thr Gly Phe Pro Phe Asp Pro His Tyr Val Glu Val Leu
        195                 200                 205

Gly Glu Arg Met His Tyr Val Asp Val Gly Pro Arg Asp Gly Thr Pro
    210                 215                 220

Val Leu Phe Leu His Gly Asn Pro Thr Ser Ser Tyr Val Trp Arg Asn
225                 230                 235                 240

Ile Ile Pro His Val Ala Pro Thr His Arg Cys Ile Ala Pro Asp Leu
                245                 250                 255

Ile Gly Met Gly Lys Ser Asp Lys Pro Asp Leu Gly Tyr Phe Phe Asp
            260                 265                 270

Asp His Val Arg Phe Met Asp Ala Phe Ile Glu Ala Leu Gly Leu Glu
        275                 280                 285

Glu Val Val Leu Val Ile His Asp Trp Gly Ser Ala Leu Gly Phe His
    290                 295                 300
```

| Trp | Ala | Lys | Arg | Asn | Pro | Glu | Arg | Val | Lys | Gly | Ile | Ala | Phe | Met | Glu |
| --- | --- | --- | --- | --- | --- | --- | --- | --- | --- | --- | --- | --- | --- | --- | --- |
| 305 | | | | 310 | | | | | 315 | | | | | 320 | |

| Phe | Ile | Arg | Pro | Ile | Pro | Thr | Trp | Asp | Glu | Trp | Pro | Arg | Asp | Gln | Leu |
| --- | --- | --- | --- | --- | --- | --- | --- | --- | --- | --- | --- | --- | --- | --- | --- |
| | | | | 325 | | | | | 330 | | | | | 335 | |

| Thr | Glu | Glu | Gln | Ile | Ala | Glu | Phe | Lys | Glu | Ala | Phe | Ser | Leu | Phe | Asp |
| --- | --- | --- | --- | --- | --- | --- | --- | --- | --- | --- | --- | --- | --- | --- | --- |
| | | | 340 | | | | | 345 | | | | | 350 | | |

| Lys | Asp | Gly | Asp | Gly | Thr | Ile | Thr | Thr | Lys | Glu | Leu | Gly | Thr | Val | Met |
| --- | --- | --- | --- | --- | --- | --- | --- | --- | --- | --- | --- | --- | --- | --- | --- |
| | | 355 | | | | | 360 | | | | | 365 | | | |

| Arg | Ser | Leu | Gly | Gln | Asn | Pro | Thr | Glu | Ala | Glu | Leu | Gln | Asp | Met | Ile |
| --- | --- | --- | --- | --- | --- | --- | --- | --- | --- | --- | --- | --- | --- | --- | --- |
| | 370 | | | | | 375 | | | | | 380 | | | | |

| Asn | Glu | Val | Asp | Ala | Asp | Gly | Asn | Gly | Thr | Ile | Asp | Phe | Pro | Glu | Phe |
| --- | --- | --- | --- | --- | --- | --- | --- | --- | --- | --- | --- | --- | --- | --- | --- |
| 385 | | | | 390 | | | | | 395 | | | | | 400 | |

| Leu | Thr | Met | Met | Ala | Arg | Lys | Met | Lys | Asp | Thr | Asp | Ser | Glu | Glu | Glu |
| --- | --- | --- | --- | --- | --- | --- | --- | --- | --- | --- | --- | --- | --- | --- | --- |
| | | | | 405 | | | | | 410 | | | | | 415 | |

| Ile | Arg | Glu | Ala | Phe | Arg | Val | Phe | Asp | Lys | Asp | Gly | Asn | Gly | Tyr | Ile |
| --- | --- | --- | --- | --- | --- | --- | --- | --- | --- | --- | --- | --- | --- | --- | --- |
| | | | | 420 | | | | | 425 | | | | | 430 | |

| Ser | Ala | Ala | Glu | Leu | Arg | His | Val | Met | Thr | Asn | Leu | Gly | Glu | Lys | Leu |
| --- | --- | --- | --- | --- | --- | --- | --- | --- | --- | --- | --- | --- | --- | --- | --- |
| | | | 435 | | | | | 440 | | | | | 445 | | |

| Thr | Asp | Glu | Glu | Val | Asp | Glu | Met | Ile | Arg | Glu | Ala | Asp | Ile | Asp | Gly |
| --- | --- | --- | --- | --- | --- | --- | --- | --- | --- | --- | --- | --- | --- | --- | --- |
| | 450 | | | | | 455 | | | | | 460 | | | | |

| Asp | Gly | Gln | Val | Asn | Tyr | Glu | Glu | Phe | Val | Gln | Met | Met | Thr | Ala | Lys |
| --- | --- | --- | --- | --- | --- | --- | --- | --- | --- | --- | --- | --- | --- | --- | --- |
| 465 | | | | 470 | | | | | 475 | | | | | 480 | |

<210> SEQ ID NO 9
<211> LENGTH: 1470
<212> TYPE: DNA
<213> ORGANISM: Artificial
<220> FEATURE:
<223> OTHER INFORMATION: Synthetic chemigenetic calcium indicator

<400> SEQUENCE: 9

| | | |
| --- | --- | --- |
| gtgcgggtta ttcccagact tgatacccctg atactcgtga aagcaatggg ccaccgaaaa | 60 |
| cgattcggta accccttttag gcctaaggag accttccagg ccttccgcac caccgacgtc | 120 |
| ggccgcaagc tgatcatcga tcagaacgtt tttatcgagg gtacgctgcc gatgggtgtc | 180 |
| gtccgcccgc tgactgaagt cgagatggac cattaccgcg agccgttcct gaatcctgtt | 240 |
| gaccgcgagc cactgtggcg cttcccaaac gagctgccaa tcgccggtga gccagcgaac | 300 |
| atcgtcgcgc tggtcgaaga atacatggac tggctgcacc agtcccctgt cccgaagctg | 360 |
| ctgttctggg gcaccccagg cgttctgatc ccaccggccg aagccgctcg cctggccaaa | 420 |
| agcctgccta actgcaaggc tgtggacatc ggcccgggtc tgaatctgct gcaagaagac | 480 |
| aacccggacc tgatcggcag cgagatcgcg cgctggctgt cgacgctcga gatttccggc | 540 |
| ggaggaacag tggttctggt ggaacaggg ggtagcggag gtacaggagg aagtatggcg | 600 |
| gagatcggaa ctggattccc gtttgatccg cattatgtgg aagttctggg agagcgcatg | 660 |
| cattatgtgg acgttggtcc tcgtgatggg acaccagtgc tgttccttca cggcaatccg | 720 |
| acatcgtcgt acgtgtggcg taatatcatc ccgcacgttg cccccaagca ccgctgcatt | 780 |
| gcccctgact taattggtat ggggaaaagt gataagcctg atctggggta cttctttgac | 840 |
| gaccacgtac gcttcatgga tgcttttatt gaagcattgg gttggagga agtagttttg | 900 |
| gtgatccatg attggggtag tgctctgggg ttccattggg ccaagcgtaa cccagaacgc | 960 |
| gtgaaaggaa ttgcctttat ggagttcatc cgtccgattc aacatggga cgaatggcct | 1020 |
| tttgcacgcg atcaattaac agaggaacag attgcggagt ttaaggaagc gttctctttta | 1080 |

```
tttgataagg atggcgacgg tacaatcact actaaagaat tgggaacagt catgcgctca    1140
ttggggcaaa atccgacaga ggctgaattg caggacatga ttaacgaggt agacgccgat    1200
gggaacggga ctatcgactt ccggaatttt cttactatga tggcacgcaa aatgaaagat    1260
accgattctg aagaagagat ccgtgaagct ttccgtgttt ttgataaaga tgggaacggc    1320
tacatcagtg ctgctgagtt acgccatgtg atgacaaatc tgggggaaaa acttaccgac    1380
gaagaagtag acgaaatgat tcgcgaggcg atattgacg gggatggaca agtaaactac      1440
gaggaatttg tgcagatgat gaccgccaag                                    1470
```

<210> SEQ ID NO 10
<211> LENGTH: 490
<212> TYPE: PRT
<213> ORGANISM: Artificial
<220> FEATURE:
<223> OTHER INFORMATION: Synthetic chemigenetic calcium indicator

<400> SEQUENCE: 10

```
Val Arg Val Ile Pro Arg Leu Asp Thr Leu Ile Leu Val Lys Ala Met
1               5                   10                  15

Gly His Arg Lys Arg Phe Gly Asn Pro Phe Arg Pro Lys Glu Thr Phe
            20                  25                  30

Gln Ala Phe Arg Thr Thr Asp Val Gly Arg Lys Leu Ile Ile Asp Gln
        35                  40                  45

Asn Val Phe Ile Glu Gly Thr Leu Pro Met Gly Val Val Arg Pro Leu
    50                  55                  60

Thr Glu Val Glu Met Asp His Tyr Arg Glu Pro Phe Leu Asn Pro Val
65                  70                  75                  80

Asp Arg Glu Pro Leu Trp Arg Phe Pro Asn Glu Leu Pro Ile Ala Gly
                85                  90                  95

Glu Pro Ala Asn Ile Val Ala Leu Val Glu Glu Tyr Met Asp Trp Leu
            100                 105                 110

His Gln Ser Pro Val Pro Lys Leu Leu Phe Trp Gly Thr Pro Gly Val
        115                 120                 125

Leu Ile Pro Pro Ala Glu Ala Ala Arg Leu Ala Lys Ser Leu Pro Asn
    130                 135                 140

Cys Lys Ala Val Asp Ile Gly Pro Gly Leu Asn Leu Leu Gln Glu Asp
145                 150                 155                 160

Asn Pro Asp Leu Ile Gly Ser Glu Ile Ala Arg Trp Leu Ser Thr Leu
                165                 170                 175

Glu Ile Ser Gly Gly Thr Gly Gly Ser Gly Gly Thr Gly Gly Ser
            180                 185                 190

Gly Gly Thr Gly Gly Ser Met Ala Glu Ile Gly Thr Gly Phe Pro Phe
        195                 200                 205

Asp Pro His Tyr Val Glu Val Leu Gly Glu Arg Met His Tyr Val Asp
    210                 215                 220

Val Gly Pro Arg Asp Gly Thr Pro Val Leu Phe Leu His Gly Asn Pro
225                 230                 235                 240

Thr Ser Ser Tyr Val Trp Arg Asn Ile Ile Pro His Val Ala Pro Lys
                245                 250                 255

His Arg Cys Ile Ala Pro Asp Leu Ile Gly Met Gly Lys Ser Asp Lys
            260                 265                 270

Pro Asp Leu Gly Tyr Phe Phe Asp Asp His Val Arg Phe Met Asp Ala
        275                 280                 285

Phe Ile Glu Ala Leu Gly Leu Glu Glu Val Val Leu Val Ile His Asp
```

|   |   |   | 290 |   |   |   | 295 |   |   |   | 300 |   |   |
|---|---|---|---|---|---|---|---|---|---|---|---|---|---|

Trp Gly Ser Ala Leu Gly Phe His Trp Ala Lys Arg Asn Pro Glu Arg
305                 310                 315                 320

Val Lys Gly Ile Ala Phe Met Glu Phe Ile Arg Pro Ile Pro Thr Trp
                325                 330                 335

Asp Glu Trp Pro Phe Ala Arg Asp Gln Leu Thr Glu Glu Gln Ile Ala
            340                 345                 350

Glu Phe Lys Glu Ala Phe Ser Leu Phe Asp Lys Asp Gly Asp Gly Thr
        355                 360                 365

Ile Thr Thr Lys Glu Leu Gly Thr Val Met Arg Ser Leu Gly Gln Asn
    370                 375                 380

Pro Thr Glu Ala Glu Leu Gln Asp Met Ile Asn Glu Val Asp Ala Asp
385                 390                 395                 400

Gly Asn Gly Thr Ile Asp Phe Pro Glu Phe Leu Thr Met Met Ala Arg
                405                 410                 415

Lys Met Lys Asp Thr Asp Ser Glu Glu Glu Ile Arg Glu Ala Phe Arg
            420                 425                 430

Val Phe Asp Lys Asp Gly Asn Gly Tyr Ile Ser Ala Ala Glu Leu Arg
        435                 440                 445

His Val Met Thr Asn Leu Gly Glu Lys Leu Thr Asp Glu Glu Val Asp
    450                 455                 460

Glu Met Ile Arg Glu Ala Asp Ile Asp Gly Asp Gly Gln Val Asn Tyr
465                 470                 475                 480

Glu Glu Phe Val Gln Met Met Thr Ala Lys
                485                 490

<210> SEQ ID NO 11
<211> LENGTH: 1464
<212> TYPE: DNA
<213> ORGANISM: Artificial
<220> FEATURE:
<223> OTHER INFORMATION: Synthetic chemigenetic calcium indicator

<400> SEQUENCE: 11
gtgcgggtta ttcccagact tgatacccctg atactcgtga aagcaatggg ccaccgaaaa      60
cgattcggta acccctttag gcgggagacc ttccaggcct ccgcaccac cgacgtcggc      120
cgcaagctga tcatcgatca gaacgttttt atcgagggta cgctgccgat gggtgtcgtc      180
cgcccgctga ctgaagtcga gatggaccat taccgcgagc cgttcctgaa tcctgttgac      240
cgcgagccac tgtggcgctt cccaaacgag ctgccaatcg ccggtgagcc agcgaacatc      300
gtcgcgctgg tcgaagaata catggactgg ctgcaccagt cccctgtccc gaagctgctg      360
ttctggggca ccccaggcgt tctgatccca ccggccgaag ccgctcgcct ggccaaaagc      420
ctgcctaact gcaaggctgt ggacatcggc ccgggtctga atctgctgca agaagacaac      480
ccggacctga tcgcagcga gatcgcgcgc tggctgtcga cgctcgagat ttccggcgga      540
ggaacaggtg gttctggtgg aacagggggt agcggaggta caggaggaag tatggcggag      600
atcggaactg gattcccgtt tgatccgcat tatgtggaag ttctgggaga gcgcatgcat      660
tatgtggacg ttggtcctcg tgatgggaca ccagtgctgt tccttcacgg caatccgaca      720
tcgtcgtacg tgtggcgtaa tatcatcccg cacgttgccc ccacgcaccg ctgcattgcc      780
cctgacttaa ttggtatggg gaaaagtgat aagcctgatc tggggtactt ctttgacgac      840
cacgtacgct tcatggatgc ttttattgaa gcattgggtt tggaggaagt agttttggtg      900
atccatgatt ggggtagtgc tctggggttc cattgggcca agcgtaaccc agaacgcgtg      960

-continued

```
aaaggaattg cctttatgga gttcatccgt ccgattccaa catgggacga atgggccgca    1020
cgcgatcaat taacagagga acagattgcg gagtttaagg aagcgttctc tttatttgat    1080
aaggatggcg acggtacaat cactactaaa gaattgggaa cagtcatgcg ctcattgggg    1140
caaaatccga cagaggctga attgcaggac atgattaacg aggtagacgc cgatgggaac    1200
gggactatcg actttccgga atttcttact atgatggcac gcaaaatgaa agataccgat    1260
tctgaagaag agatccgtga agctttccgt gtttttgata agatgggaa cggctacatc     1320 agtgctgctg agttacgcca tgtgatgaca atctggggg aaaaacttac cgacgaagaa     1380
gtagacgaaa tgattcgcga ggcggatatt gacggggatg gacaagtaaa ctacgaggaa    1440
tttgtgcaga tgatgaccgc caag                                           1464
```

<210> SEQ ID NO 12
<211> LENGTH: 488
<212> TYPE: PRT
<213> ORGANISM: Artificial
<220> FEATURE:
<223> OTHER INFORMATION: Synthetic chemigenetic calcium indicator

<400> SEQUENCE: 12

```
Val Arg Val Ile Pro Arg Leu Asp Thr Leu Ile Leu Val Lys Ala Met
1               5                   10                  15

Gly His Arg Lys Arg Phe Gly Asn Pro Phe Arg Arg Glu Thr Phe Gln
            20                  25                  30

Ala Phe Arg Thr Thr Asp Val Gly Arg Lys Leu Ile Ile Asp Gln Asn
        35                  40                  45

Val Phe Ile Glu Gly Thr Leu Pro Met Gly Val Val Arg Pro Leu Thr
    50                  55                  60

Glu Val Glu Met Asp His Tyr Arg Glu Pro Phe Leu Asn Pro Val Asp
65                  70                  75                  80

Arg Glu Pro Leu Trp Arg Phe Pro Asn Glu Leu Pro Ile Ala Gly Glu
                85                  90                  95

Pro Ala Asn Ile Val Ala Leu Val Glu Glu Tyr Met Asp Trp Leu His
            100                 105                 110

Gln Ser Pro Val Pro Lys Leu Leu Phe Trp Gly Thr Pro Gly Val Leu
        115                 120                 125

Ile Pro Pro Ala Glu Ala Ala Arg Leu Ala Lys Ser Leu Pro Asn Cys
    130                 135                 140

Lys Ala Val Asp Ile Gly Pro Gly Leu Asn Leu Leu Gln Glu Asp Asn
145                 150                 155                 160

Pro Asp Leu Ile Gly Ser Glu Ile Ala Arg Trp Leu Ser Thr Leu Glu
                165                 170                 175

Ile Ser Gly Gly Gly Thr Gly Gly Ser Gly Gly Thr Gly Gly Ser Gly
            180                 185                 190

Gly Thr Gly Gly Ser Met Ala Glu Ile Gly Thr Gly Phe Pro Phe Asp
        195                 200                 205

Pro His Tyr Val Glu Val Leu Gly Glu Arg Met His Tyr Val Asp Val
    210                 215                 220

Gly Pro Arg Asp Gly Thr Pro Val Leu Phe Leu His Gly Asn Pro Thr
225                 230                 235                 240

Ser Ser Tyr Val Trp Arg Asn Ile Ile Pro His Val Ala Pro Thr His
                245                 250                 255

Arg Cys Ile Ala Pro Asp Leu Ile Gly Met Gly Lys Ser Asp Lys Pro
            260                 265                 270
```

```
Asp Leu Gly Tyr Phe Asp Asp His Val Arg Phe Met Asp Ala Phe
        275                 280                 285
Ile Glu Ala Leu Gly Leu Glu Val Val Leu Val Ile His Asp Trp
    290                 295                 300
Gly Ser Ala Leu Gly Phe His Trp Ala Lys Arg Asn Pro Glu Arg Val
305                 310                 315                 320
Lys Gly Ile Ala Phe Met Glu Phe Ile Arg Pro Ile Pro Thr Trp Asp
                325                 330                 335
Glu Trp Ala Ala Arg Asp Gln Leu Thr Glu Glu Gln Ile Ala Glu Phe
                340                 345                 350
Lys Glu Ala Phe Ser Leu Phe Asp Lys Asp Gly Asp Gly Thr Ile Thr
                355                 360                 365
Thr Lys Glu Leu Gly Thr Val Met Arg Ser Leu Gly Gln Asn Pro Thr
370                 375                 380
Glu Ala Glu Leu Gln Asp Met Ile Asn Glu Val Asp Ala Asp Gly Asn
385                 390                 395                 400
Gly Thr Ile Asp Phe Pro Glu Phe Leu Thr Met Met Ala Arg Lys Met
                405                 410                 415
Lys Asp Thr Asp Ser Glu Glu Glu Ile Arg Glu Ala Phe Arg Val Phe
                420                 425                 430
Asp Lys Asp Gly Asn Gly Tyr Ile Ser Ala Ala Glu Leu Arg His Val
                435                 440                 445
Met Thr Asn Leu Gly Glu Lys Leu Thr Asp Glu Glu Val Asp Glu Met
    450                 455                 460
Ile Arg Glu Ala Asp Ile Asp Gly Asp Gly Gln Val Asn Tyr Glu Glu
465                 470                 475                 480
Phe Val Gln Met Met Thr Ala Lys
                485

<210> SEQ ID NO 13
<211> LENGTH: 6
<212> TYPE: PRT
<213> ORGANISM: Artificial
<220> FEATURE:
<223> OTHER INFORMATION: Linker

<400> SEQUENCE: 13

Gly Gly Ser Gly Gly Thr
1               5
```